United States Patent
Themelis

(10) Patent No.: US 11,422,345 B2
(45) Date of Patent: Aug. 23, 2022

(54) ARM ADAPTED TO BE ATTACHED TO A MICROSCOPE, AND MICROSCOPE

(71) Applicant: LEICA INSTRUMENTS (SINGAPORE) PTE. LTD., Singapore (SG)

(72) Inventor: George Themelis, Lindau (DE)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 497 days.

(21) Appl. No.: 16/269,647

(22) Filed: Feb. 7, 2019

(65) Prior Publication Data

US 2019/0250384 A1 Aug. 15, 2019

(30) Foreign Application Priority Data

Feb. 9, 2018 (EP) ..................................... 18156144

(51) Int. Cl.
| G02B 21/00 | (2006.01) |
| A61B 90/20 | (2016.01) |
| G02B 21/36 | (2006.01) |
| A61B 90/50 | (2016.01) |
| A61B 90/00 | (2016.01) |
| G02B 21/06 | (2006.01) |
| A61B 17/00 | (2006.01) |
| G02B 26/10 | (2006.01) |
| G02B 21/22 | (2006.01) |

(52) U.S. Cl.
CPC .............. *G02B 21/00* (2013.01); *A61B 90/20* (2016.02); *A61B 90/361* (2016.02); *A61B 90/37* (2016.02); *A61B 90/50* (2016.02); *G02B 21/06* (2013.01); *G02B 21/362* (2013.01); *A61B 2017/00123* (2013.01); *A61B 2090/367* (2016.02); *A61B 2090/371* (2016.02); *G02B 21/0012* (2013.01); *G02B 21/22* (2013.01); *G02B 26/105* (2013.01)

(58) Field of Classification Search
CPC .... G02B 21/00; G02B 21/0012; G02B 21/06; G02B 21/362; G02B 21/22; G02B 23/24; G02B 26/105; A61B 90/20; A61B 90/361; A61B 90/37; A61B 90/50; A61B 2090/367; A61B 2090/371; A61B 2017/00123
See application file for complete search history.

(56) References Cited

U.S. PATENT DOCUMENTS

| 2004/0223213 A1 | 11/2004 | Fukuyama et al. |
| 2004/0249247 A1 | 12/2004 | Iddan |
| 2008/0200764 A1 | 8/2008 | Okada |
| 2013/0038689 A1 | 2/2013 | McDowell |

(Continued)

FOREIGN PATENT DOCUMENTS

| CN | 102736239 A | 10/2012 |
| CN | 203841666 U | 9/2014 |

(Continued)

*Primary Examiner* — Darryl J Collins
*Assistant Examiner* — Tamara Y. Washington
(74) *Attorney, Agent, or Firm* — Hodgson Russ LLP

(57) ABSTRACT

The invention relates to an arm (1) adapted to be attached to a microscope (10), in particular a surgical microscope (10), wherein the arm (1) comprises at a distal end (21) a light beam deflection member (3) or a camera. An inventive microscope (10) comprises an arm (1).

15 Claims, 2 Drawing Sheets

(56) References Cited

U.S. PATENT DOCUMENTS

| | | | |
|---|---|---|---|
| 2013/0140412 A1* | 6/2013 | Hirose | A61B 90/50 248/124.1 |
| 2016/0030021 A1* | 2/2016 | Pasternak | A61B 10/0275 600/424 |
| 2017/0020627 A1 | 1/2017 | Tesar et al. | |
| 2017/0181802 A1 | 6/2017 | Sachs et al. | |
| 2017/0273549 A1* | 9/2017 | Nazareth | A61B 90/361 |
| 2017/0351072 A1* | 12/2017 | Ku | G02B 21/0012 |
| 2018/0049642 A1* | 2/2018 | Mak | G01B 9/02091 |
| 2018/0122333 A1 | 5/2018 | Horiike | G06F 3/017 |
| 2019/0059869 A1* | 2/2019 | Avalos | A61B 90/30 |

FOREIGN PATENT DOCUMENTS

| | | |
|---|---|---|
| CN | 104837397 A | 8/2015 |
| CN | 106308944 A | 1/2017 |
| DE | 4116810 A1 | 11/1992 |
| JP | S50-038387 A | 4/1975 |
| JP | S63-158303 U | 10/1988 |
| JP | H05-253246 A | 10/1993 |
| JP | H06-261913 A | 9/1994 |
| JP | H08131455 A | 5/1996 |
| JP | H09-016755 A | 1/1997 |
| JP | 2004-344201 A | 12/2004 |
| JP | 2009-297416 A | 12/2009 |
| JP | 2011113028 A | 6/2011 |
| JP | 2013-048693 A | 3/2013 |
| WO | 2017132745 A1 | 8/2017 |

* cited by examiner

ARM ADAPTED TO BE ATTACHED TO A MICROSCOPE, AND MICROSCOPE

CROSS REFERENCE TO RELATED APPLICATIONS

This application claims priority of European patent application number 18156144.0 filed Feb. 9, 2018, the entire disclosure of which is incorporated by reference herein.

FIELD OF THE INVENTION

The invention relates to the field of microscopes, in particular surgical microscopes.

BACKGROUND OF THE INVENTION

Such microscopes are often used to inspect the operation area at which surgery is performed. In many cases, it is necessary to not only have an overview of the operation area but also of the neighboring area, for example of a cavity in which surgery takes place. In current solutions, the microscope is removed from the operation area and an endoscope is used in its stead to get an overview. This is however time-consuming and cumbersome.

SUMMARY OF THE INVENTION

It is the object of the invention to provide a solution that is more time efficient, easy to use, more intuitive, requires very little or no training, and could be safer.

According to the invention, this is achieved by an arm adapted to be attached to a microscope, in particular a surgical microscope, wherein the arm comprises at a distal end at least one of a light beam deflection member or a camera.

When the arm is attached to the microscope, the surgeon no longer has to remove the microscope from the operation area and insert an endoscope. Rather, the arm can be used with the arm already in place to inspect the area neighboring the operation area. The distal end is to be understood as the end that is opposite a proximal end where the arm is attached to the microscope.

A microscope according to the invention comprises an arm according to the invention.

The inventive solution can be improved by the following further improvements and advantageous embodiments, which are advantageous on their own and can be combined arbitrarily as desired.

For example, the at least one light beam deflection member or camera may be rotatable around at least one axis. This allows the inspection of a wide spherical area.

The arm can comprise a bearing that allows a rotation of the light beam deflection member or the camera around the axis. In a compact design, the bearing can be located within the arm.

The arm or the microscope can comprise a drive system to drive the rotation of the light beam deflection member or the camera. The drive system can for example comprise a motor or a piezo drive to rotate the light beam deflection member. The drive system can be integrated into the arm or be remote from the arm.

In an alternative or in addition, the microscope can comprise a bearing that allows a rotation of the entire arm around the axis relative to the rest of the microscope.

In a further embodiment, at least two cameras may be provided, wherein the optical axes of said cameras are different. Therefore, an inspection of a wide area is possible without the need of a rotatable camera. Preferably at least four cameras may be provided, wherein the cameras can be positioned in a cross formation, so that each camera is showing away from the opposing camera. This allows the inspection of a wide area.

In an advantageous development, the light beam deflection member can be a mirror. This can be simple to manufacture and to operate.

In an alternative, the light beam deflection member can comprise a prism, a fiber or any device in which the input direction of the light differs from the output direction. Such a solution can be easy to implement.

In an advantageous development, the light beam deflection member or the camera can be rotatable around at least two axes. This allows an inspection of a wider spherical area. Ideally, the rotation around the at least two axes allows an inspection of an entire spherical area ($4\pi$) or an area that is close to an entire spherical area.

The arm can comprise a camera module, a field of view of the camera module being directed to the light beam deflection member. In such a solution, the light beam does not have to be directed through long areas and an adjustment of the beam path is easy. Further, the modifications necessary to the rest of the microscope are of minor nature as most of the additional devices are located in the arm.

In an alternative, the arm can be hollow. This allows to guide the light beam through the hollow arm. The camera module can be located in another part of the microscope. This can for example allow for an easy interchangeability of an arm. Further, the arm can be lighter. No obstruction of the light path can take place.

In order to allow a closer inspection of the neighboring area, the arm can comprise a magnification assembly for the camera module or the camera. The magnification assembly can comprise lenses.

In an advantageous development, the arm can comprise at least one collision detector that is adapted to detect a contact with a tissue. Thereby, it can be avoided that the arm damages sensitive tissue when it is being moved.

Such a collision detector, or at least parts of it, can be located at the distal end of the arm, in particular at a front end to detect a contact when the arm is being moved towards the patient. In addition or in an alternative, the collision detector or parts of it can be located at a side of the arm to avoid a contact when the arm is being moved sideways.

The collision detector can comprise a touch sensor that detects when something comes in direct mechanical contact with the arm. Such an embodiment can be easy to manufacture and implement.

In a further embodiment, the collision detector can comprise a hardware or software module. The hardware or software module can be adapted to detect a contact or collision based on data from other modules or units. It can be adapted to detect a collision based on for example currents that are used to drive the arm. If the arm contacts something, the driving current can increase as the control unit can try to move the arm despite the obstacle. The module can detect this increase and deduct that a collision has taken place.

The collision detector or the microscope can be adapted to provide an alarm signal in case of a contact. Such an alarm signal can either be an acoustic or visual signal that can be perceived by a surgeon so that he or she can take countermeasures. The alarm signal can also be a signal that is provided to other parts of the microscope, for example a control unit of the microscope so that countermeasures are taken automatically by the control unit. For instance, a further movement of the arm along the movement direction can be blocked and/or the arm can automatically be retracted at least slightly when the alarm signal is on.

In order to avoid collisions, the arm can comprise at least one proximity detector that is adapted to measure and evaluate the proximity to the tissue. Thereby, damages to sensitive tissue when the arm is being moved can be avoided.

Such a proximity detector, or at least parts of it, can be located at the distal end of the arm, in particular at a front end to measure and evaluate the proximity to the tissue when the arm is being moved towards the patient. In addition or in an alternative, the proximity detector or parts of it can be located at a side of the arm to measure and evaluate the proximity of the arm to the tissue when said arm is being moved sideways.

In a further embodiment, the proximity detector can comprise a hardware or software module. The hardware or software module can be adapted to detect the proximity of the arm to the tissue based on data from other modules or units. The hardware or software module of the proximity detector may define different sections of proximity between the arm and the tissue.

The proximity detector or the microscope can be adapted to provide an alarm signal in case of a close proximity of the arm to the tissue. Such an alarm signal can either be an acoustic or visual signal that can be perceived by a surgeon so that he or she can take countermeasures. The alarm signal may be different for different proximity zones, wherein for example in close proximity the alarm may give a different signal than in a proximity zone with a larger distance between the arm and the tissue. The alarm signal can also be a signal that is provided to other parts of the microscope, for example a control unit of the microscope so that countermeasures are taken automatically by the control unit. For instance, a further movement of the arm along the movement direction can be blocked and/or the arm can automatically be retracted at least slightly when the alarm signal is on. Furthermore, the speed of the movement may be automatically reduced upon close proximity of the arm to the tissue.

The proximity detector and the collision detector may be separate detectors or in an alternate embodiment one detector may be a feature of the other detector.

The proximity detector can comprise an ultrasonic member, a laser member, a radar-like member or a capacitive detector to allow an efficient and fast detection.

In order to allow a better inspection, the arm can comprise an illumination device. The illumination device can in particular be located at the distal end to achieve a good illumination. It can also be attached to or integrated into a camera module or a camera to keep the arm compact.

The illumination device can in addition or in an alternative be adapted for illuminating the operation area where surgery is performed. This makes further illumination devices unnecessary.

The illumination device can be adapted to illuminate a field of view of the camera module to give the surgeon a good view of the neighboring area.

The arm can at least in sections be elastically deformable around at least one axis that is essentially perpendicular to the longitudinal axis of the arm. Therefore, injury risks through collision of the arm with the tissue may be reduced.

The arm may be elastically deformable by the force applied upon contact with for example the tissue, so that the damage to the tissue is reduced compared to the contact with a rigid arm.

In another advantageous embodiment, the arm can be elastically deformed manually by the user, giving the user more control in exactly positioning the arm and therefore, reducing the risk of contact with the tissue.

Additionally or in an alternative embodiment, the arm can be elastically deformed around at least one axis that is essentially perpendicular to the longitudinal axis of the arm automatically depending on the proximity of the arm to the tissue. Therefore, the contact between the arm and the tissue may be avoided, since the arm will automatically be elastically deformed away from the tissue upon close proximity.

Preferably, the arm can be elastically deformed around at least two axes which are essentially perpendicular to one another and are both arranged essentially perpendicular to the longitudinal axis of the arm.

In order to facilitate the deformation, the arm can comprise a deformation device. The deformation device can comprise force generating members like motors and/or Piezo elements or force transmitting members like gears or cables.

In an advantageous development, the arm comprises a 3D-scanning member for creating a 3D-image of the operation area where surgery is to be performed. This allows the surgeon to have a better overview of the entire region. In an advantageous embodiment, the camera is configured to as the 3D-scanning member.

The 3D-scanning member can be located at a distal end of the arm so that the 3D-image of the cavity can be taken efficiently.

The 3D-scanning member can comprise an ultrasonic member, a laser member or radar-like member to allow an efficient and fast scanning.

Advantageously, two sensors of the 3D-scanning member are spaced apart from each other. In this manner, the 3D-image can be created easily.

A 3D-image may be or include a stereoscopic image. Therefore, it is possible to display the image on a 2D screen creating the illusion of 3D depth.

A 3D-image may include a z-axis measurement, giving the user a perception of depth in a 2D image.

A 3D-image may include a spherical image around the imaging position. Therefore a wide image of the surroundings is provided without a blind angle.

The proximity detector and the 3D-scanning member may be separate detectors or in an alternate embodiment one detector may be a feature of the other detector. In an advantageous development, the arm can be a telescopic arm. By this, the distal end can be moved through a telescoping of the arm and no movement of other parts of the microscope is necessary.

In an alternative, or in addition, the arm can be movable together with other parts of the microscope, in particular the rest of the microscope. This can allow a simple design and control.

In a further alternative, the arm can be movable relative to other parts of the microscope, in particular the rest of the microscope. The arm could be moved into and out of a body of the microscope. Such a design can be easier to implement.

Advantageously, the microscope can be adapted to control a rotation of the light beam deflection device or the camera. This can make the operation simpler, for example compared to a manual rotation of the light beam deflection device or the camera.

The microscope can for example comprise a control module for rotating the beam deflection device or the camera. This module can comprise hardware or software. It can be integrated into a control module for the entire microscope, in order to keep the construction simple.

In an advantageous development, the microscope may comprise a motion controller for controlling a movement of the arm and/or a rotation of the light beam deflection member or the camera. This can allow a simple control by the user. The motion controller can for example comprise a joystick for an intuitive control.

In another advantageous embodiment, the microscope may comprise microscope handles that may function as a motion controller, wherein the movements of the handles is replicated by the imaging axis determining the field of view. This makes the orientation for the surgeon easier.

A separate motion controller for adjusting the elastic deformation of the arm may be provided. The microscope can comprise a positioning device adapted to move the arm relative to the rest of the microscope in at least one direction. This allows the positioning of the arm in a simple manner.

The positioning device can comprise an X-Y-stage that allows a positioning in a plane perpendicular to an extension direction of the arm. The position device can further comprise a drive for a z-movement that means a movement in an extension direction of the arm.

In order to keep the construction compact, the arm can be located at a center of a beam path of the microscope.

In another embodiment, the arm can be arranged parallel to the longitudinal axis of the beam path of the microscope. This solution can be simple and effective.

Alternatively, the arm can be arranged in an angle to the longitudinal axis of the beam path of the microscope. This can allow an accessibility of areas that are difficult to view.

The microscope can comprise an image processing module for collecting and merging images taken along different rotational orientations into a spherical image or a 3D-image of the operation area and/or the neighboring area. This simplifies the orientation as the user can then view a spherical image or a 3D-image of the neighboring area and/or the operation area.

Similarly, the microscope can comprise a module adapted to collect data taken by the 3D-scanning member and to merge them into a spherical image or a 3D-image of the operation area and/or the neighboring area. Again, this makes the orientation for the surgeon easy.

In an advantageous development, a position detector can be provided that provides data representative of the rotational position of the arm. By this, the rotational position can be known at all times. The rotational position can for example be a rotational position of the arm relative to the microscope or relative to other references. The positioning device can be located on the arm or on the microscope.

The microscope can comprise an image processing module, wherein the image processing module is adapted to add directional information into an image. The surgeon can then see from the image in which direction this images is taken.

The directional information can be based on control or positional information of the arm or the microscope, for example from a position detector. The directional information can be referenced to a reference direction.

The directional information can be a numerical angular value, for example two angles relative to a reference direction.

In an alternative, the directional information can be verbal information like left, right, dorsal or the like, to make the operation for the surgeon easier.

The image processing module can be adapted to merge further information into the image like information obtained by fluoroscopy, to simplify the operation.

In order to give the surgeon an intuitive way of exploring the neighboring area, the microscope can comprise a visualization device providing a virtual reality experience.

A retrofit kit can comprise at least an arm according to the invention. Such a retrofit kit can be used to turn a regular microscope into a microscope according to the invention. The arm can therefore comprise interfaces like mechanical interfaces and/or electrical or electronic interfaces. these interfaces can in particular be a standardized according to industry or internal standards. For example, a mechanical interface can comprise a plate and/or fixation members, wherein the configuration of the plate and/or the fixation members is standardized. Electrical or electronic interfaces can comprise plugs and sockets that can be standardized.

In the following, the inventive solutions will be explained in more detail and with reference to the drawings. The features shown in the further developments and advantageous embodiments can be combined as desired and are advantageous on their own.

BRIEF DESCRIPTION OF THE DRAWING VIEWS

In the Figs.

DETAILED DESCRIPTION OF THE INVENTION

Figure 1:
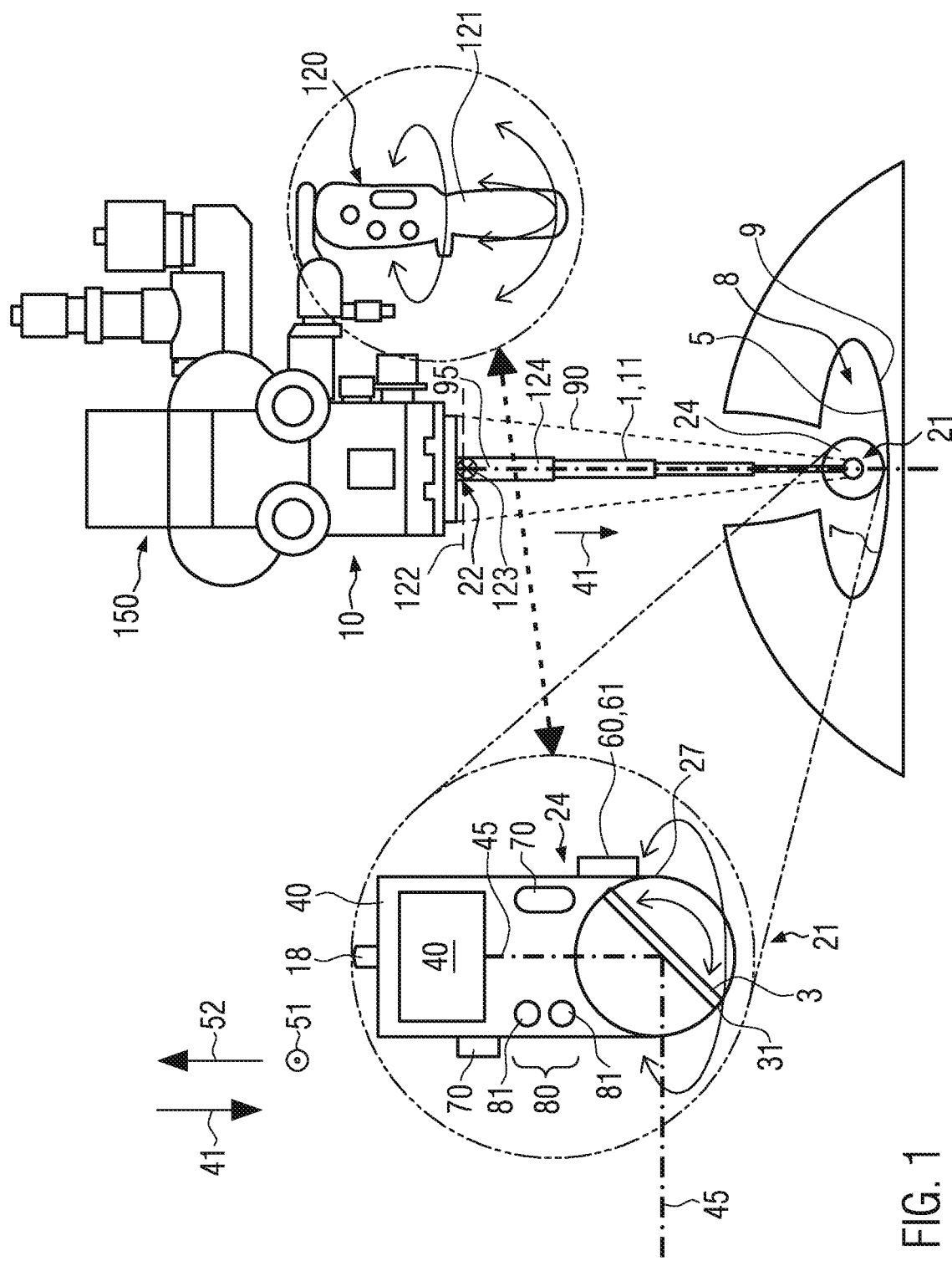
FIG. 1 shows a schematic view of an embodiment of a microscope.

In FIG. 1, an arm 1 is attached to a microscope 10. The microscope 10 is used as a surgical microscope 10 to inspect an operation area 5, for example inside a human head during brain surgery. The operation area 5 is in direct line of sight of optics of the microscope 10. However, for the surgeon it is also important to be able to look at a neighboring area 9 next to the operation area 5. Conventionally, the microscope is removed and an endoscope is used to look at the neighboring area 9. However, due to the inventive solution, it is possible to look at the neighboring area 9 without removing the microscope 10.

The arm 1 comprises at a distal end 21 that is opposite a proximal end 22 at which the arm 1 is attached to the microscope 10, a light beam deflection member 3 that is rotatable around at least one axis 51, 52. In the embodiment of FIG. 1, the rotatable light beam deflection member 3 is rotatable around two axes 51, 52, one of which is parallel to an extension direction 41 of the arm 1 and the other one of which is perpendicular to the extension direction 41.

The arm 1 comprises bearings 27 (shown only schematically) to allow the rotation of the light beam deflection member 3 relative to the rest of the arm 1. Further, the arm 1 comprises a non-depicted drive system to drive a rotation of the light beam deflection member 3.

The light beam deflection member 3 is embodied as a mirror 31, but could also take other forms. It can for example be a prism or a fibre that redirects the light beam.

The arm 1 further comprises a camera module 40. The field of view 45 of the camera module 40 is directed onto the light beam deflection member 3 and then redirected sideways. The fact that the camera module 40 is located in the arm 1 makes the design simple. In other designs, however, the camera module 40 could be located in other parts of the microscope 10. For example, the arm 1 can be a hollow arm 1 and the field of view 45 of the camera module 40 can be guided through the hollow arm 1 and the camera module 40 can be located at an upper part of the microscope 10 outside the arm 1.

The arm 1 can comprise a magnification assembly (not shown in detail) for the camera module 40 to allow a closer inspection of the neighboring area 9.

The arm 1 can be part of a retrofit kit that allows to upgrade a prior art microscope into a microscope according to the invention. To achieve this, interfaces like mechanical interfaces or electric or electronic interfaces can be standardized according to industry or internal standards. The retrofit kit can for example additionally comprise adapters.

The arm 1 also comprises a collision detector 60 that is partially located on a side 24 of the arm 1. The collision detector 60 serves to detect a potentially damaging contact with a tissue 7. The collision detector 60 can also be located at a front surface at the distal end 21 to detect a contact for example when the arm 1 is moved towards the operation area 5.

The collision detector 60 can output an alarm signal in case of a contact. This alarm signal can give the surgeon a direct feedback, for example through an acoustic or a visual alarm signal. The alarm signal can also be processed in other parts of the microscope 10, in particular a control unit of the microscope 10. The control unit can then automatically stop a movement of the arm 1 or the microscope 10 or cause a retraction of the arm 1 or the microscope 10.

The arm 1 may also comprises a proximity detector 61 that is partially located on a side 24 of the arm 1. The proximity detector 61 serves to measure and evaluate the proximity of the arm 1 to a tissue 7. The proximity detector 61 can also be located at a front surface at the distal end 21 to measure and evaluate the proximity for example when the arm 1 is moved towards the operation area 5. The proximity detector 61 may be an additional feature of the collision detector 60 and vice versa.

The collision detector 60 and/or proximity detector 61 can output an alarm signal in case of a contact or close proximity respectively. This alarm signal can give the surgeon a direct feedback, for example through an acoustic or a visual alarm signal. The alarm signal can also be processed in other parts of the microscope 10, in particular a control unit of the microscope 10. The control unit can then automatically stop a movement of the arm 1 or the microscope 10 or cause a retraction of the arm 1 or the microscope 10.

The proximity detector 61 may have defined different proximity sections which are segmented according to the distance between the arm 1 and the tissue 7, wherein the alarm signal differs according to the proximity section. For example, in case of a visual alarm signal the color of the alarm signal may change upon close proximity of the arm 1 to the tissue 7 or the frequency of an acoustic alarm signal can be raised, giving the surgeon a direct feedback. Upon close proximity the control unit can automatically reduce the speed of a movement of the arm 1 or the microscope 10.

An illumination device 70 can serve to provide light to the operating area 5 and/or the neighboring area 9.

The arm 1 comprises a 3D-scanning member 80 for creating a 3D-image of the operation area 5 and the neighboring area 9. The 3D-scanning member 80 therefore comprises two sensors 81 that are spaced apart from each other in an extension direction 41 of the arm 1. The sensors 81 can for example be laser sensors, radar sensors or ultrasonic sensors.

The proximity detector 61 may be an additional feature of the 3D-scanning member 80 and vice versa.

The arm 1 is in this embodiment a telescopic arm 11 so that the distal end 21 of the arm 1 and thus the light beam deflection member 3 can be moved along the extension direction 41 of the arm without moving the microscope 10 or the entire arm 1. Rather, parts of the telescopic arm 11 can be moved relative to other parts of the telescopic arm 11 and in particular slide into and out of the other parts.

In a non-depicted other embodiment, the arm 1 could be a single element, for instance a single rod. The arm 1 could then for example be moved into and moved out of other parts of the microscope to achieve a movement along the extension direction 41. In a further embodiment, the arm could be moved together with the microscope 10.

In order to keep the construction compact, the arm 1 is located at a centre 95 of the beam path 90 of the microscope 10, wherein the longitudinal axis 124 of the arm is essentially parallel to the beam path 90. It is possible to simultaneously take microscopic images with the microscope 10 and images of the neighboring area 9 through the camera module 40 and the rotatable light beam deflection member 3.

The microscope 10 is adapted to control a rotation of the light beam deflection device 3. It comprises a control module 150 and motion controller 120 which comprises a joystick 121. The motion controller 120 can be used to control the rotation of the light beam deflection member 3 in an intuitive manner.

The arm 1 may be elastically deformable around at least two axes 122, 123 that are essentially perpendicular to one another and are both arranged essentially perpendicular to the longitudinal axis 124 of the arm 1. Therefore, the risk of an injury due to collision of the arm 1 with the tissue 7 is further reduced. The elastic deformation of the arm 1 may be adjusted by the motion controller 120.

In a non-depicted embodiment, a separate motion controller for adjusting the elastic deformation of the arm may be provided.

In a non-depicted embodiment, a rotatable camera could be used instead of the rotatable light beam deflection member 3.

Figure 2:
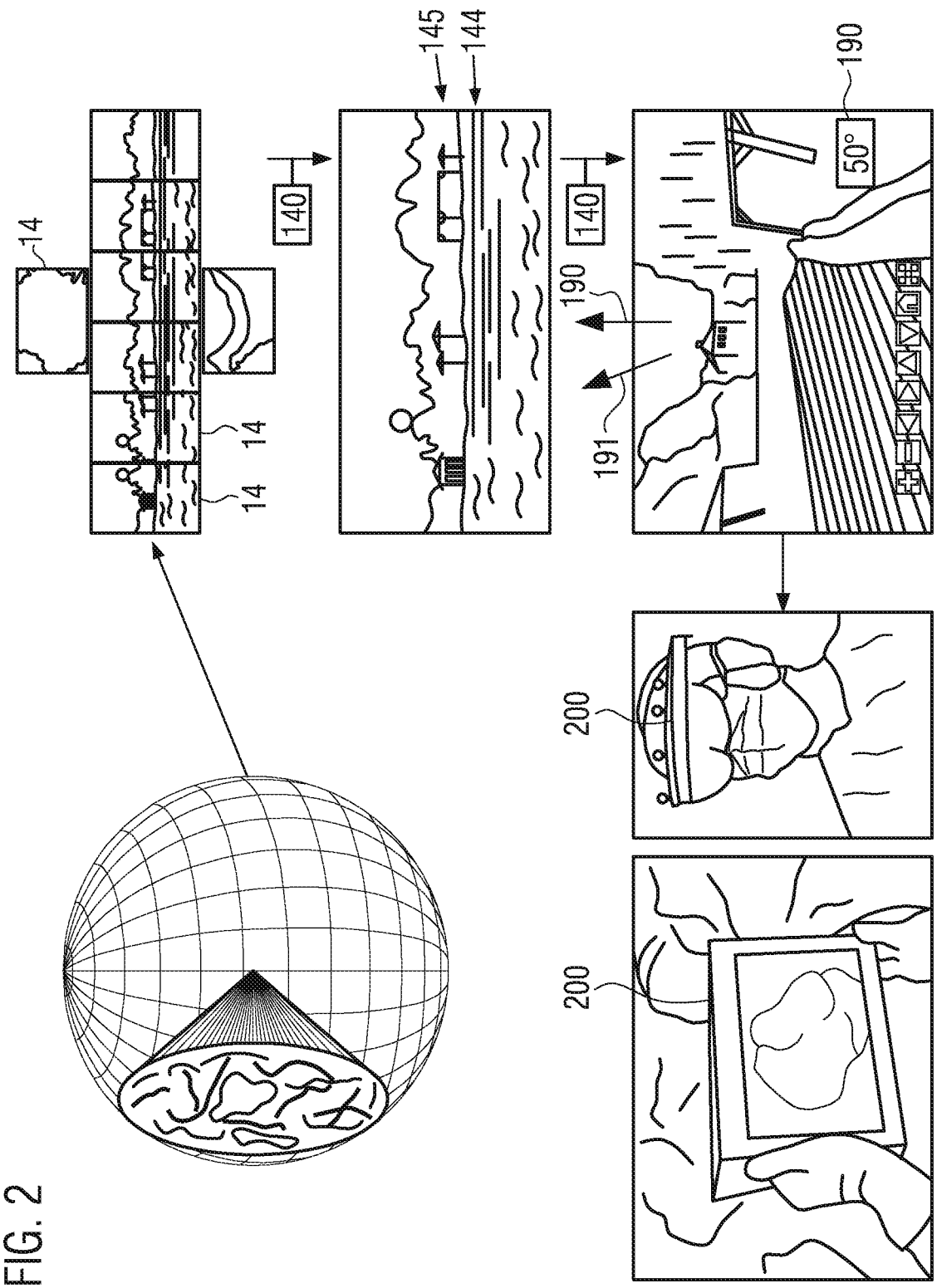
FIG. 2 shows a schematic diagram of the creation of a spherical or 3D-image and the viewing of this by a surgeon.

In FIG. 2, it is shown how the inventive solution can be used to give a surgeon a good overview of the operation area 5 and the neighboring area 9. The camera module 40 takes several images 14 at different rotational directions for example to the left and the right and up and down. These images are merged or stitched together by an image processing module 140 so that a spherical image 144 or 3D-image 145 of the operation area 5 and the neighboring area 9 is created.

The image processing module 140 can also add directional information 190, for example arrows or numerical values to give the surgeon information in which direction the image is taken, for example relative to a reference direction 191. The relative position of the field of view 45 of the camera 40 can be detected by a position detector 18 (see FIG. 1) that for example detects the relative position of the arm 1 relative to the rest of the microscope 10.

Similarly, the image processing module 100 can use 3D-data obtained by the 3D-scanning member 80 in order to create a 3D-image or a 3D-model or a spherical image of the operation area 5 and the neighboring area 9. The image processing module 140 can also combine the data from the 3D-scanning member 80 and the images 14 taken by the camera module 40.

The image processing module 140 can in a non-depicted embodiment also merge further information or images obtained for example by fluoroscopy into the image 14 to make the operation easier.

The microscope can also comprise a visualisation device 200, for example in the form of a virtual reality set that provides a virtual reality experience. The surgeon 200 can then experience the operation area 5 and the neighboring area 9 by rotating the head. Alternatively or in addition, the visualisation device 200 can for example be a tablet.

REFERENCE NUMERALS 1 arm
3 light beam deflection member
5 operation area
7 tissue
8 cavity
10 microscope
11 telescopic arm
14 image
18 position detector
21 distal end
22 proximal and
24 side
27 bearing
31 mirror
40 camera module
41 extension direction
45 field of view
51 axis
52 axis
60 collision sensor
61 proximity sensor
70 illumination device
80 3D-scanning member
81 sensor
90 beam path
95 centre
120 motion controller
121 joystick
122 axis
123 axis
124 longitudinal axis
130 positioning device
140 image processing module
144 spherical image
145 3D-image
150 control module
190 directional information
191 reference direction
200 visualisation device

What is claimed is:

1. An arm adapted to be attached to a microscope, the arm comprising:
   a distal end; and
   at least one of a light beam deflection member at the distal end and a camera at the distal end;
   wherein the light beam deflection member or the camera is configured to capture images of a neighboring area of an operation area outside of a beam path of the microscope.

2. The arm according to claim 1, wherein the light beam deflection member or the camera is rotatable around at least one axis.

3. The arm according to claim 1, wherein the arm comprises the light beam deflection member and the camera, and wherein the arm further comprises a camera module including the camera and having a field of view, wherein the field of view of the camera module is directed to the light beam deflection member.

4. The arm according claim 1, further comprising at least one collision detector adapted to detect a contact with a tissue and/or at least one proximity detector adapted to measure and evaluate the proximity to the tissue.

5. The arm according to claim 1, wherein the arm is elastically deformable around at least one axis that is essentially perpendicular to a longitudinal axis of the arm.

6. The arm according to claim 1, further comprising an illumination device.

7. The arm according to claim 1, further comprising a 3D-scanning member for creating a 3D-image of an operation area where surgery is to be performed and/or a neighboring area of the operation area.

8. The arm according to claim 1, wherein the arm is a telescopic arm.

9. A microscope apparatus comprising:
   a microscope configured to capture images of an operation area inside a beam path of the microscope;
   an arm attached to the microscope, wherein the arm comprises a distal end and at least one of a light beam deflection member at the distal end and a camera at the distal end;
   wherein the light beam deflection member or the camera is configured to capture images of a neighboring area of the operation area outside of the beam path of the microscope.

10. The microscope apparatus according to claim 9, wherein the microscope is adapted to control a rotation of the light beam deflection device or the camera.

11. The microscope apparatus according to claim 9, wherein the microscope comprises a motion controller for controlling a movement of the arm and/or a rotation of the beam deflection member or the camera.

12. The microscope apparatus according to claim 9, wherein the arm is located at a center of a beam path of the microscope.

13. The microscope apparatus according to claim 9, wherein the microscope comprises an image processing module for collecting and merging images taken along different rotational orientations into a spherical image or a 3D image of an operation area and/or a neighboring area of the operation area.

14. The microscope apparatus according to claim 9, wherein the microscope comprises an image processing module wherein the image processing module is adapted to add directional information into an image.

15. The microscope apparatus according to claim 9, wherein the microscope comprises a visualization device providing a virtual reality experience.

* * * * *